United States Patent [19]

Reddy

[11] Patent Number: 5,082,004
[45] Date of Patent: Jan. 21, 1992

[54] PROPHYLACTIC WITH GLANS PENIS STIMULATION

[76] Inventor: Alla V. K. Reddy, 9 Webster Ct., Plainsboro, N.J. 08536

[21] Appl. No.: 545,905

[22] Filed: Jun. 29, 1990

Related U.S. Application Data

[63] Continuation-in-part of Ser. No. 526,843, May 22, 1990, Pat. No. 5,027,831.

[51] Int. Cl.$^5$ .............................................. A61F 6/04
[52] U.S. Cl. .................... 128/844; 128/918
[58] Field of Search ................ 128/79, 842, 844, 918; 604/330, 347–353

[56] References Cited

U.S. PATENT DOCUMENTS

| | | | |
|---|---|---|---|
| 2,326,159 | 8/1943 | Mendel | 128/157 |
| 2,365,556 | 12/1944 | Karg | 128/844 |
| 2,577,345 | 12/1951 | McEwen | 604/349 |
| 3,136,417 | 6/1964 | Clinch | 128/844 |
| 3,759,254 | 9/1973 | Clark | 128/844 |
| 4,795,425 | 1/1989 | Pugh | 128/844 |
| 4,852,586 | 8/1989 | Haines | 128/844 |
| 4,919,149 | 4/1990 | Stang | 128/842 |
| 4,961,734 | 10/1990 | Kassman | 128/844 |
| 4,966,165 | 10/1990 | Anderson | 128/844 |
| 4,977,903 | 12/1990 | Haines | 128/844 |

FOREIGN PATENT DOCUMENTS 2620729 11/1977 Fed. Rep. of Germany .
0859835 12/1940 France .

Primary Examiner—Robert A. Hafer
Assistant Examiner—Michael Brown
Attorney, Agent, or Firm—Reising, Ethington, Barnard, Perry & Milton

[57] ABSTRACT

A male prophylactic which has a tubular pouch with a closed end and an open end and an integrally formed pouch or pouches on the tubular pouch at the closed end defining a spaced pouch or pouches on the tubular pouch adjacent to the glans penis. The pouch or pouches on the tubular pouch are configured to be movable back and forth in the area of the glans penis from approximately ½ cm below the urethra orifice to a point approximately 2 cm approximately from the orifice. The pouch or pouches on the tubular pouch do not bind the glans penis to restrict sensitivity and allow the relative movement between the vaginal wall and glans penis to be more readily sensed, thereby stimulating the glans penis during coitus. In one embodiment, discrete pouches are spaced longitudinally along the tubular pouch. The foremost of these pouches serves to stimulate the glans penis, while the rearmost of these pouches functions to massage and stimulate the female partner's clitois during coitus.

36 Claims, 3 Drawing Sheets

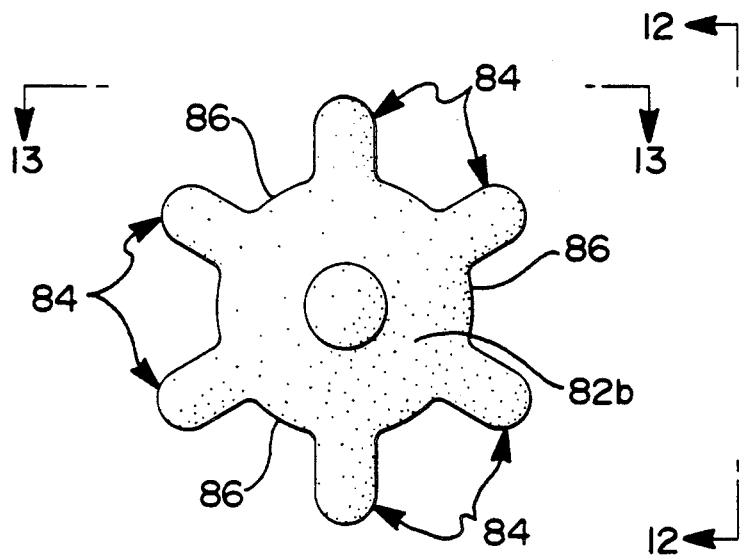
FIG 11
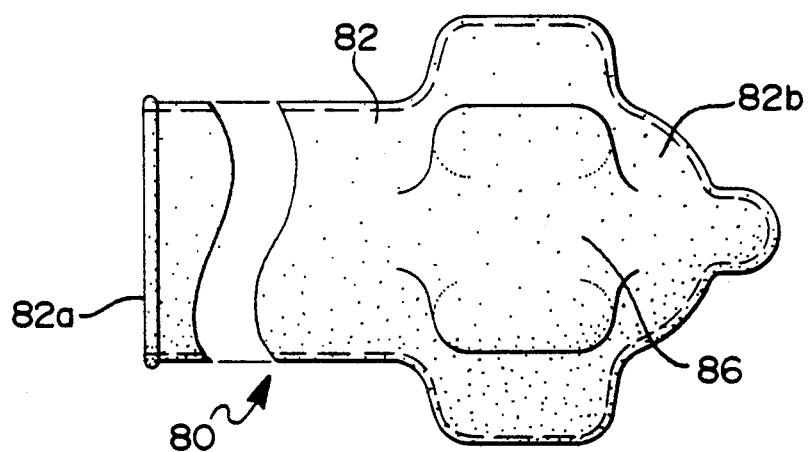
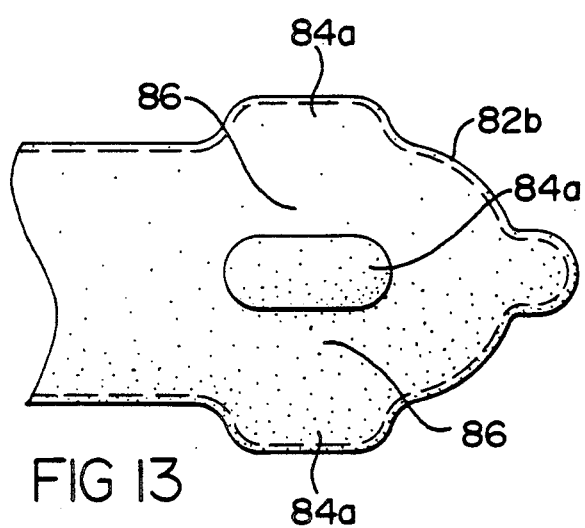
FIG 13

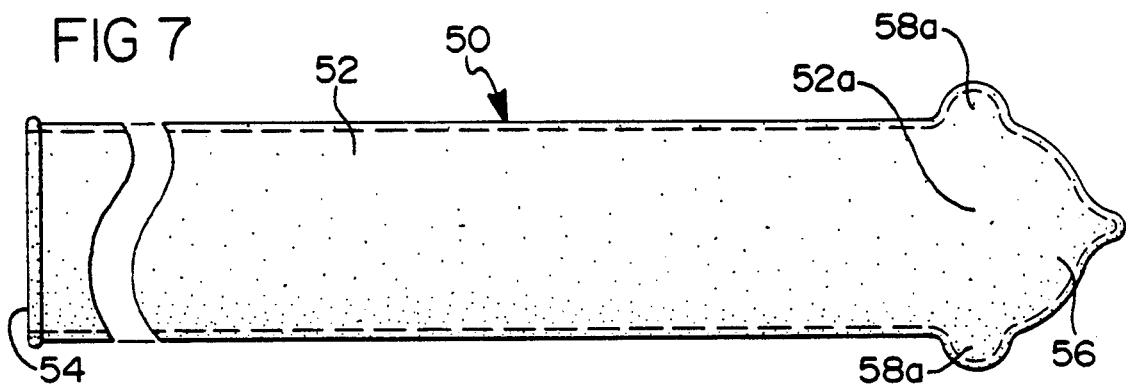
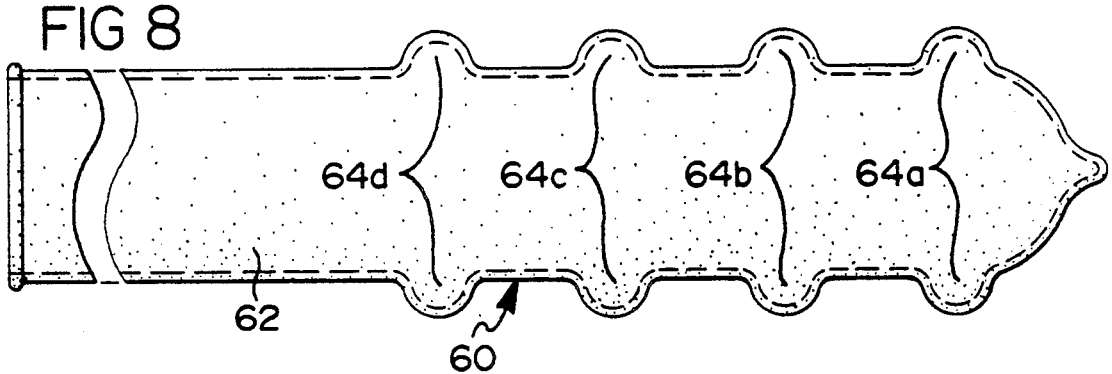
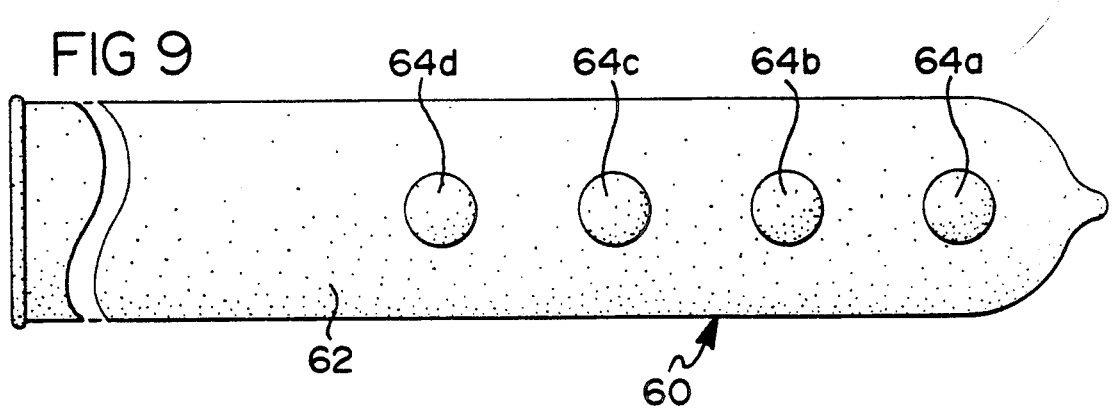
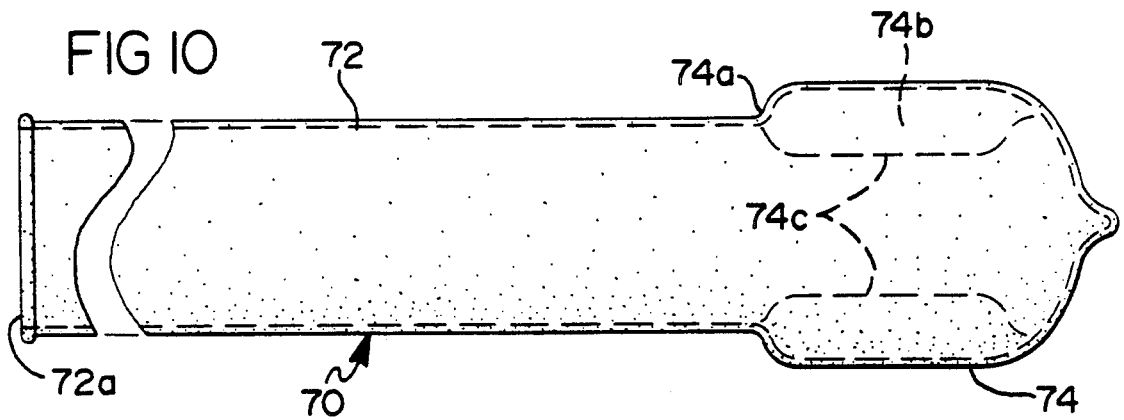

PROPHYLACTIC WITH GLANS PENIS STIMULATION

This is a continuation-in-part application of U.S. Ser. No. 526,843 filed May 22, 1990. Now U.S. Pat. No. 5,027,831.

FIELD OF THE INVENTION

This invention relates to prophylactic or birth control devices and in particular to such devices designed for the male partner in coitus.

BACKGROUND OF THE PRIOR ART

A wide variety of male condoms or prophylactic devices are known for use in disease prevention and to safeguard against pregnancy. In the past such devices have been tight fitting to prevent accidental dislodgment during coitus. Furthermore, in order to be rupture proof the wall thickness of membrane material forming the pouch of such male condoms has resulted in loss of sensation by the male user during coitus. Also, tight fitting condoms bind the glans penis resulting in restricted sensitivity and loss of stimulation during coitus.

Other loose fitting condoms have been proposed for female use including U.S. Pat. Nos. 4,004,591 and 3,536,066. Both of these patents disclose pouches of a diameter much larger than that of the glans penis and they do not include pouch on pouch means capable of producing stimulation of the surface of a glans penis during coitus. Also, in the above patents, the condoms cover the vaginal wall rather than the penis.

U.S. Pat. No. 2,816,542 discloses a condom with a thickened wall portion at the condom tip for stimulation.

U.S. Pat. No. 254,808 issued Apr. 22, 1980 discloses an ornamental design in which the pouch of a male condom has outwardly directed bulges. However, the bulges are not arranged so as to stimulate the surface of a glans penis during coitus.

Another approach has been to provide male condoms with ultra-thin walls, e.g., wall thickness of 0.03 mm. Such condoms have been manufactured and sold in Japan in recognition of the increase in sensitivity to the male user. Such ultra thin condoms, however, are more susceptible to leakage or tearing, which makes them less suitable when considering protection against life threatening diseases such as Acquired Immune Deficiency Syndrome (AIDS). Furthermore, even the ultra thin condoms fit tightly and bind the glans penis, resulting in restricted sensitivity and loss of stimulation during coitus.

None of the aforesaid condoms include a condom with a pouch or pouches on a tubular pouch arranged to produce a rubbing action on the most sensitive region of the glans penis. Furthermore, none of the aforesaid condoms provide a condom which has a wall thickness on the order of up to four times the thickness of the ultra-thin variety of condoms while retaining equivalent sensitivity or greater sensitivity.

STATEMENT OF INVENTION AND ADVANTAGES

The AIDS epidemic has caused more people to consider the use of condoms for protection against transmission of AIDS and other social diseases. Prior condoms, however, have resulted in less sensation and, as a consequence, their use is often omitted. The purpose of this invention is to provide an improved condom which will be more acceptable to male users and, therefore, more widely used because of increased user sensation.

It is an object of the present invention to provide a male condom which will be more acceptable to the male user by providing enhanced sensation during coitus and enhanced tactile stimulation during foreplay.

In order to solve the problem of insensitivity the condom of the present invention is configured to take advantage of the recognized greater sensitivity of the glans penis during coitus.

To this end, the condom includes a pouch or pouches on the tubular pouch in the thin membrane material of the condom that will move back and forth on the underside region of the glans penis or in areas adjacent to and encircling the glans penis during coitus to provide enhanced stimulation and sensitivity to the male user of the condom.

A feature of the present invention is to solve the insensitivity problem in male condoms by providing an elongated tubular pouch or pouches of thin membrane material formed on the circumference of the closed end to form a pocket or pockets overlying in spaced relationship to the glans penis and movable back and forth thereon during coitus for providing stimulation thereto.

A further feature is to provide such pouch on pouch means formed through only a part of the circumference to produce movement only on part of the surface of the glans penis, e.g., the underside of the glans penis or in areas adjacent to an encircling the glans penis.

A still further feature is to provide such pouch or pouches on pouch means formed on the circumference of the closed end completely around the circumference to produce movement on all of the surface of the glans penis.

Yet another feature of the invention is to provide such a condom in which the pouch is formed of fine rubber or plastic material and the pouch or pouches on pouch means is formed as a side bulge in the circumference of the closed end.

A further feature of the invention is to provide such a condom wherein the pouch is characterized by the side bulge being formed as a hollow shaped bulge.

Yet another feature of the present invention is to provide such a condom wherein the pouch is characterized by the side bulge being formed as a hollow ring around the closed end of the pouch.

Yet another features is to provide such a condom wherein the pouch is a single large pouch on the end of the condom to provide looseness only at the glans penis.

Still another features of the present invention is to provide greater user sensitivity in male condoms having a wall thickness in the order of 0.11 mm±0.04 mm by providing loose end portion at the glans penis which will roll to rub the glans penis to increase stimulation thereof.

Still another feature is to provide the male condom of the preceding summary wherein the pouch on pouch or loose end portion is filled with a water soluble or other lubricant to produce a hydrodynamic rubbing action on the glans penis for increasing sensitivity during coitus.

Still another feature is to provide a male condom as set forth wherein the loose end portion is defined by a plurality of intermediate wall lengths to maintain the condom diameter and circumferentially located and spaced pouches which provide looseness at the glans penis.

Still another feature is to provide such a male condom in which a plurality of spaced pouches are located longitudinally of the condom to provide both stimulation of the glans penis and concurrent massage and stimulation of the clitoris during coitus.

Yet another feature of the present invention is to provide a condom wherein the pouch or pouches cannot be eliminated if the user stretches the condom too tightly along the length of the penis as the condom is placed on the penis. Areas of material between the pouches are of the same diameter as the proximal shaft of the condom (open end of condom) and restrict longitudinal stretching which might tend to reduce or eliminate the pouch or pouches.

Other advantages of the present invention will be readily appreciated as the same becomes better understood by reference to the following detailed description when considered in connection with the accompanying drawings wherein:

BRIEF DESCRIPTION OF THE DRAWINGS

FIG. 7 is a side view of a two pouch on pouch embodiment;

FIG. 8 is a side view of an embodiment with longitudinally spaced pouches;

FIG. 9 is a front view of the embodiment of FIG. 8;

FIG. 10 is a single pouch embodiment of the present invention;

FIG. 11 is an end elevational view of another embodiment of this invention featuring circumferentially spaced pouches;

FIG. 12 is a side view looking in the direction of arrow 12 in FIG. 11; and

FIG. 13 is a top view looking in the direction of arrow 13 in FIG. 11.

DETAILED DESCRIPTION OF PREFERRED EMBODIMENTS

Figure 1:
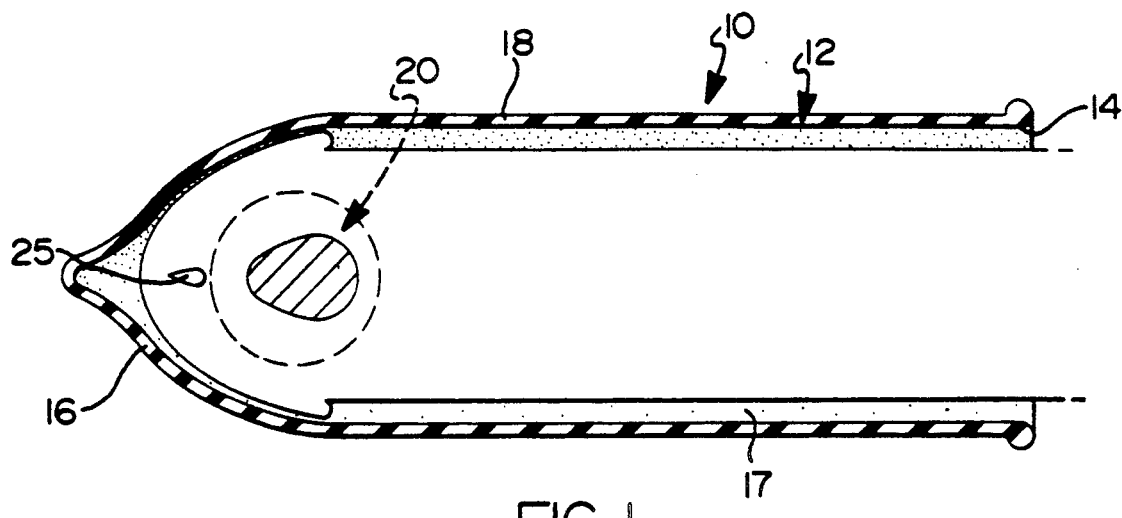
FIG. 1 is a sectional view of a male condom including one embodiment of the present invention.
Figure 2:
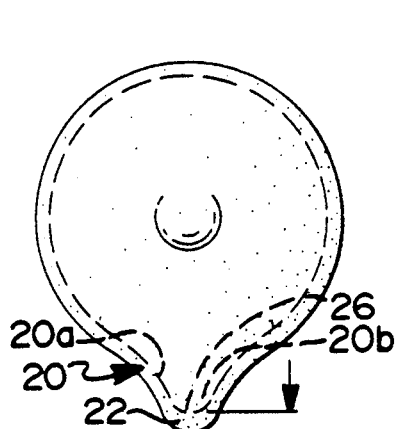
FIG. 2 is an end elevational view of the male condom of FIG. 1.

FIGS. 1 and 2 illustrate a male condom 10 having a tubular pouch 12 with an open end 14 and a closed end 16. The pouch 12 has a diameter which will closely fit on the outer surface of a penis whose glans penis will be located within the pouch in spaced relationship to the closed end 16 to define a longitudinally directed chamber 17. The pouch 12 is of generally constant diameter between the open end 14 and the closed end 16. The pouch 12 has a thin membrane wall 18 that will enhance sensation to the male user during use but which will retain enough strength to prevent rupture of the wall 18 during use for protection against AIDS and other sexually transmitted diseases.

In accordance with certain principles of the present invention the pouch 12 includes a glans penis pouch on pouch 20 which in the embodiment of FIGS. 1 and 2 is in the form of a wall bulge 22. The pouch 20 has an entrance opening 20a through which the chamber 17 is communicated with an interior space 20b of the pouch 20. The wall bulge 22 is located in one side of the pouch 12 at a point overlying and in spaced relationship to the most sensitive surface 24 of the glans penis, starting approximately ½ cm from the outlet 25 from the urethra and ending at a point 2 cm from the outlet 25, as shown in shaded outline in FIG. 1.

Figure 3:
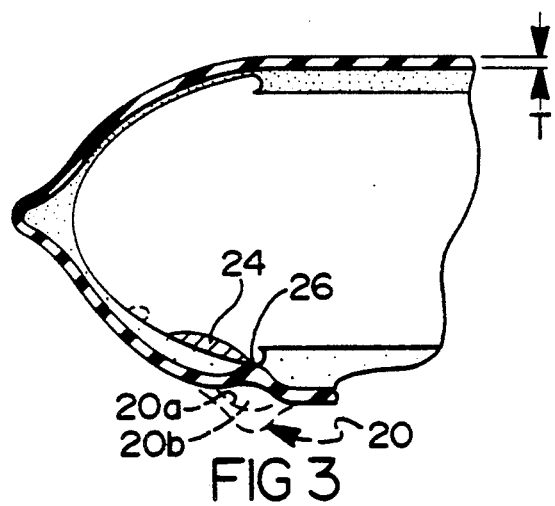
FIG. 3 is a fragmentary sectional view of the condom of FIGS. 1 and 2 showing a pouch on pouch stroked inwardly.

Specifically, the wall bulge 22 has a conoidal surface 26 which will be pushed inwardly during coitus to move back and forth on the glans penis surface 24 as shown in the enlarged fragmentary sectional view of FIG. 3. The back and forth movement will stimulate the glans penis so as to provide enhanced sensation to the male user of the condom 10. While the pouch on pouch 20 can have the same thickness T as the pouch wall 18, as shown in FIG. 1, the thickness of pouch on pouch 20 can also be greater.

Figure 4:
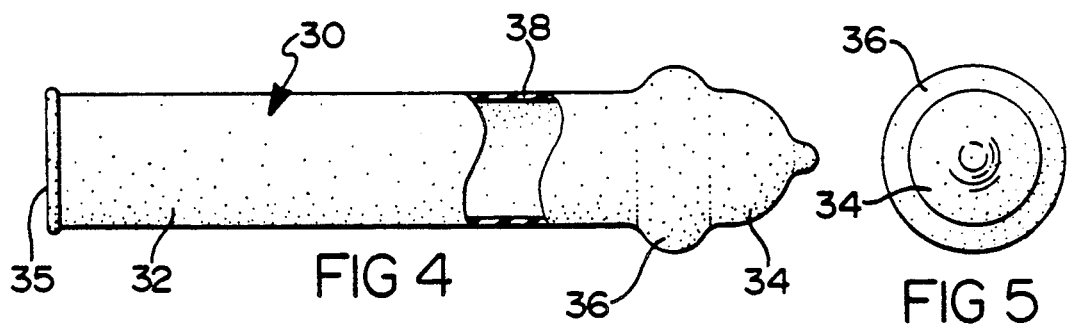
FIG. 4 is a side elevational view of a male condom including another embodiment of the present invention.
Figure 5:
FIG. 5 is an end elevational view of the male condom of FIG. 4.
Figure 6:
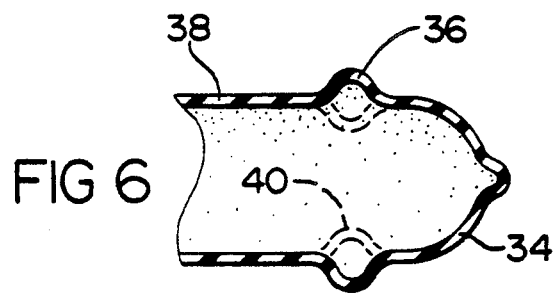
FIG. 6 is a fragmentary sectional view of the FIGS. 4 and 5 embodiment showing the pouch on pouch stroked inwardly.

In the embodiment of FIGS. 4–6 a male condom 30 is shown with a thin membrane tubular pouch 32 having a closed end 34 and an open end 36. The diameter of the pouch 32 closely fits to the outer surface of a male penis such that the glans penis is located in spaced relationship to the closed end 34.

In this embodiment the glans penis pouch on pouch is in the form of a hollow ring 36 formed integrally of the wall 38 of the pouch 32 around the circumference of the glans penis in spaced relationship therewith. During coitus a circular surface 40 of the hollow ring 36 moves back and forth on the surface 24 of the glans penis, as illustrated by broken lines in FIG. 6.

In the various embodiments of prophylactic devices of this invention, the sizes of the pouches and wall thicknesses of the materials may vary. The tubular pouch may have a length on the order of 160 mm. Although the circumference of the pouch is generally uniform, it could vary if desired. In the main body portion, the circumference is approximately 105 mm. The circumference at the pouch or pouches on the pouch is in the range of 160 mm±20 mm. However, the glans penis pouch on pouch is dimensioned to provide a space prior to insertion and a reversal of the pouch on pouch inwardly during coitus to provide a back and forth movement in engagement with the surface of the glans penis.

The thickness of the wall material of the pouch may also vary. Preferably the wall thickness is in the range of 0.11 mm–0.04 mm to 0.11 mm+0.04 mm. The pouch and entrance flange are preferably made of elastic, impermeable material such as natural rubber, synthetic rubber, such as silicone rubber. Other useful materials include plastics, such as polyurethane, polyvinyl chloride or polyethylene.

In all of the aforedescribed embodiments of the invention as well as those to be described below the pouch or pouches on pouch structure is provided so that the glans penis surface will not be tightly captured by the tubular pouch portion of the condom. What has been observed is that such tightness will dull the sensitivity of the glans penis and thereby reduce the acceptability of condom use. The present invention provides the pouch or pouches on pouch structure to produce looseness between the inside surface of the tubular pouch and the outer surface of the glans penis. Such looseness in turn maintains a high level of surface sensitivity on the glans penis. While the greatest sensitivity is on the underside of the glans penis, the other parts of the glans penis surface are also sensitive to rubbing action of the pouch or pouches on pouch portions of the invention.

A further feature of the invention is produced by providing a sufficient quantity of a suitable water soluble lubricant in the tubular pouch such that the pouch or pouches on pouch will be coated with the lubricant. The lubricant in the hollow interior of the pouch or pouches on pouch facilitates the in and out rubbing action of the pouch or pouches on pouch against the outer surface of the glans penis and produce a hydrodynamic flushing of the outer surface of the glans penis to enhance the stimulation thereof during coitus.

The increase in sensitivity attributable to the pouch or pouches on pouch looseness, rubbing and the aforedescribed hydrodynamic action all combine to enable the wall thickness of a condom to be increased to thickness in the order of 0.11 mm plus or minus 0.04 mm, while maintaining sensitivity equal to or greater than that found in ultra thin condoms having a wall thickness of 0.03 mm. The greater thickness provides strength against rupture or tearing, which is important in the protection of a user against life-threatening diseases.

Referring now to the embodiment of FIG. 7, a male prophylactic 50 is shown having a tubular pouch 52 with an open end 54 and a closed end 56. A pair of diametrically opposite pouch on pouch portions 58a, 58b are formed integrally of the tubular pouch 52 at the outer circumference thereof inboard of the closed end 56 so as to overlie the outer surface of a glans penis on a fully erected penis protected by the prophylactic 50. Each of the pouch on pouch portions 58a, 58b are formed as bag like members loosely spaced from the outer surface of the glans penis. As a consequence, the tubular pouch 52 will not bind the glans penis so as to reduce its sensitivity. The portions 58a, 58b can be lubricated as set forth above to provide a hydrodynamic rubbing action as the pouch on pouch portions move in and out of the tubular pouch 52 during coitus. Another aspect of the FIG. 7 embodiment is that it includes length portions 52a on the pouch 56 between each of the pouch on pouch portions 58a, 58b. These wall length portions 52a extend to the closed end 56 so as to prevent the bulge of the pouch on pouches 58a and 58b from being reduced when the condom is stretched on the penis in a longitudinal direction. The intermediate pouch on pouch portions 58a, 58b produce sufficient looseness at the glans penis for desired sensitivity which leads to wider acceptability of condom use. In an exemplary embodiment, the prophylactic will have a thickness in the range of 0.11 mm±0.04 mm without dulling sensitivity. The width of the condom is on the order of 52 mm. The length of the condom is 160 mm end to end and the distance of the pouch on pouch portions 58a, 58b is 32 mm from the closed tip 56 to the longitudinal center of the pouch on pouch portions 58a, 58b. The aforesaid dimensions are representative only, with it being understood that the width, length and location of the pouch on pouch portions will vary as required to provide the intended looseness to perform the rubbing actions of the invention on the glans penis of a user of the prophylactic 50.

The embodiment of the invention shown in FIGS. 8 and 9 is similar to the embodiment of FIG. 7 but, instead of a single pair of diametrically opposed pouch on pouch portions, a condom 60 is shown with a tubular pouch 62 having a plurality of longitudinally spaced pairs of diametrically opposed pouch on pouch portions 64a, 64b, 64c and 64d. Each of the pairs of pouch on pouch portions 64a-64d are formed on the outer circumference of the tubular pouch 62 as hollow segments which provide a looseness around the glans penis (at the pouch portions 64a and possibly 64b) and along the shaft of an erected penis (at pouch portions 64c and 64d and possibly pouch portion 6b). As in the prior embodiments, the pouch on pouch portions 64a-64d will provide a rubbing action to enhance sensation. This enables the wall thickness of the condom 60 to be increased as set forth above to increase protection. The hollows of the pouch portions 64a-64d can be lubricated, as disclosed above, to produce the desired hydrodynamic stroking action.

A condom formed as illustrated in FIGS. 8 and 9 provides an additional benefit to the female partner during coitus. Pouches 64b, 64c, and 64d slightly protrude from the shaft of the tubular portion in such a way that during intercourse the soft, flexible rubber protrusion can engage and gently stimulate the clitoris of the female partner. Protrusions 64b, 64c, and 64d are shown as pouches on a pouch, but for the purpose of clitoral stimulation, the shape of the protrusion could have any form that would gently massage and stimulate the clitoris as the penis moves back and forth.

The embodiment of the invention shown in FIG. 10 includes a condom 70 having a tubular portion 72 with a single pouch 74 formed on the end thereof with a length to overlie and provide looseness at the outer surface of a glans penis. In this embodiment, exemplary dimensions are: circumference of the tubular portion 72 on the order of 104 mm, the width of the tubular portion being 52 mm and a length of 11 cms from the open end 72a thereof to the inlet end 72a of the single pouch 74. The single pouch has a width of 80 mm±10 mm that provides a looseness around the surface of an erect glans penis which will prevent a binding action thereagainst capable of dulling its sensitivity. As in the other embodiments, the single pouch embodiment can include lubricant in the space 74b, shown in broken line in FIG. 10 within the single pouch 74. The in and out movement of the wall 74c of the single pouch 74 is depicted by broken lines in FIG. 10. Such movement is produced during in and out stroking of the condom covered penis. Such movement will cause the wall 74c to produce a hydrodynamic stroking action on the outer surface of the glans penis to produce additional stimulation for enhanced sensitivity.

Yet another embodiment of the invention is shown in FIGS. 11-13 as a condom 80 having a tubular portion 82 with an open end 82a and a closed end 82b. The tubular portion 82 is a tubular pouch on which is formed a circumferentially spaced multiple pouch on pouch array 84 inboard of the closed end 82b by a distance of about 32 mm to the centers of each of the pouch on pouch formations in the array 84. Each of the pouch on pouch formations in the array 84 are formed as slightly elongated bulges in the tubular portion 82 to define a looseness around the outer surface of a glans penis located within condom 80. Each of the bulges 84a are separated by wall segments 86 on the tubular portion 82 which extend uninterruptedly to the closed end 82a. Each of the wall segments 86 combine to maintain the shape of the tubular portion 82 with the bulges to maintain a looseness of the glans penis, by resisting undue stretching of the condom on the penis. This will maintain the sensitivity of the glans penis during coitus. As seen in FIG. 11, the pouch on pouch array 84 has a star pattern which will move in and out of the interior of the tubular portion 82 to produce the desired rubbing action and hydrodyanamic action (if lubricated) as described above.

While the invention has been described in an illustrative manner, it should be understood that the invention may be practiced other than as specifically described herein and yet remain within the scope of the appended claims.

What is claimed is:

1. A prophylactic pouch for use by a male having an elongated tubular portion forming a first pouch having a circumference and having an open end and a closed end characterized by:
    said tubular portion being formed of thin membrane material and having a generally constant diameter from the open end to the closed end to define a longitudinally directed chamber for a male penis; and
    a second pouch formed of thin membrane material extending outwardly of said first pouch; said second pouch having an interior space and including an entrance with an open area extending lengthwise of the glans penis; said entrance communicating said interior space directly with said longitudinally directed chamber at a point overlying the glans penis; said second pouch having an inner surface moveable through said entrance and against the glans penis for movement; back and forth thereon during coitus for providing stimulation thereto.

2. The prophylactic pouch of claim 1 characterized by the second pouch being formed through only a part of the circumference to produce movement only on part of the underside surface of the glans penis.

3. The prophylactic pouch of claim 2 characterized by the first pouch being formed of fine rubber or plastic material and said second pouch integrally formed with said first pouch as a side bulge in the circumference at the closed end.

4. The prophylactic pouch of claim 3 characterized by the side bulge being formed as a hollow baggy bulge having a length in excess of 1 cm.

5. The prophylactic pouch of claim 3 characterized by the side bulge being formed as a hollow ring around the closed end of said pouch.

6. The prophylactic pouch of claim 1 characterized by the second pouch being formed completely around the circumference to produce an annular pocket for movement on all of the surface of the glans penis.

7. The prophylactic pouch of claim 1 characterized by the second pouch formed as a hollow ring.

8. The prophylactic pouch of claim 1 characterized by said second pouch being formed as a single pouch on the closed end to overlie the glans penis and providing looseness between the prophylactic pouch and a penis only at the glans penis portion thereof.

9. The prophylactic pouch of claim 1 characterized by the second pouch having its inner surface coated with a lubricant to provide a hydrodynamic rubbing of the glans penis.

10. The prophylactic pouch of claim 9, characterized by the lubricant being a water soluble lubricant.

11. The prophylactic pouch of claim 1 characterized by the second pouch being filled with a water soluble lubricant to provide a hydrodynamic rubbing of the glans penis.

12. The prophylactic pouch of claim 11 characterized by the lubricant being a water soluble lubricant.

13. A prophylactic pouch for use by a male having an elongated tubular portion forming a first pouch having a circumference and having an open end and a closed end characterized by:
    said tubular portion being formed of thin membrane material and having a generally constant diameter from the open end to the closed end to define a longitudinally directed chamber for a male penis; and
    a plurality of second pouches arranged around the circumference; each of said second pouches formed of thin membrane material extending outwardly of said first pouch; each of said second pouches having an interior space and including an entrance with an open area extending lengthwise of the glans penis; said entrance communicating said interior space directly with said longitudinally directed chamber at a point overlying the glans penis; said second pouch having an inner surface moveable through said entrance and against the glans penis to produce movement thereof against the surface of the glans penis.

14. The prophylactic pouch of claim 9 characterized by the second pouches being formed around the circumference as a plurality of circumferentially spaced external pouches to produce rubbing movement on all of the surfaces of the glans penis.

15. The prophylactic pouch of claim 9 characterized by the second pouches comprising a plurality of longitudinally spaced open pouches to produce rubbing movement along the length of the surface of the glans penis and to provide clitoral stimulation during coitus.

16. The prophylactic pouch of claim 15 characterized by the second pouches being coated with a lubricant to provide a hydrodynamic rubbing of the glans penis.

17. The prophylactic pouch of claim 16 characterized by the lubricant being a water soluble lubricant.

18. A prophylactic pouch for use by a male having an elongated tubular portion forming a first pouch having a circumference and having an open end and a closed end having a tip characterized by:
    said tubular portion being formed of thin membrane material and having a generally constant diameter from the open end to the closed end;
    a plurality of second pouches formed of thin membrane material extending outwardly of said first pouch; each of said second pouches having an interior space and including an entrance with an open area extending lengthwise of the glans penis at least 1 cm; said entrance communicating said interior space directly with said longitudinally directed chamber at a point overlying the glans penis; each of said second pouches having an inner surface moveable through said entrance and against the glans penis;
    portions of said tubular portion located between each of said second pouches maintaining said constant diameter throughout the length of the tubular portion to resist stretching of said tubular portion to thereby maintain the shape of said second pouches;
    said second pouches providing looseness at the outer surface of the glans penis to increase its sensitivity to the rubbing action.

19. A prophylactic pouch for use by a male having an elongated tubular portion forming a first pouch having a circumference and having an open end and a closed end having a tip characterized by:

said tubular portion being formed of thin membrane material and having a generally constant diameter from the open end to the closed end;

a plurality of second pouches formed of thin membrane material extending outwardly of said first pouch; each of said second pouches having an interior space and including an entrance wit an open area extending lengthwise of the glans penis at least 1 cm; said entrance communicating said interior space directly with said longitudinally directed chamber at a point overlying the glans penis; each of said second pouches having an inner surface moveable through said entrance and against the glans penis for movement;

portions of said tubular portion located between each of said second pouches maintaining said constant diameter throughout the length of the tubular portion to resist stretching of said tubular portion to thereby maintain the shape of said second pouches;

said second pouches providing looseness at the outer surface of the glans penis to increase its sensitivity to the rubbing action; and said second pouches further characterized by being a plurality of circumferentially spaced pouches to produce rubbing movement on all of the surfaces of the glans penis.

20. A prophylactic pouch for use by a male having an elongated tubular portion having a circumference and an open end and a closed end having a tip characterized by:

said tubular portion being formed of thin membrane material and having a generally constant diameter from the open end to the closed end;

plural pouches integrally formed on the circumference at the closed end to produce movement on part of the surface of the glans penis;

portions of said tubular portion located between said plural pouches maintaining said constant diameter throughout the length of the tubular portion to resist stretching of said tubular portion to thereby maintain the shape of said plural pouches;

said plural pouches providing looseness at the outer surface of the glans penis to increase its sensitivity to rubbing action of said pouch on pouch means on the glans penis;

characterized by said plural pouches being filled with a lubricant to provide a hydrodynamic rubbing of the glans penis.

21. The prophylactic pouch of claim 20 characterized by the lubricant being a water soluble lubricant.

22. A prophylactic pouch for use by a male having an elongated tubular portion forming a first pouch having a circumference and having an open end and a closed end characterized by:

said tubular portion being formed of thin membrane material and having a generally constant diameter from the open end to the closed end;

a second pouch integrally formed on the circumference of the closed end for forming a loose pocket overlying in spaced relationship to the glans penis and having an inner surface movable back and forth thereon during coitus for providing stimulation thereto;

said tubular portion and said second pouch having a wall thickness of 0.11 mm ±0.04 mm; and said second pouch having its inner surface spaced radially outwardly of said tubular portion to provide looseness between said tubular portion and the outer surface of the glans penis to prevent binding of the glans penis with consequent reduction in sensitivity.

23. The prophylactic pouch of claim 22 characterized by the second pouch comprising a plurality of circumferentially spaced open pouches to produce rubbing movement on all of the surfaces of the glans penis.

24. The prophylactic pouch of claim 22 characterized by the second pouch comprising a plurality of longitudinally spaced open pouches to produce rubbing movement along the length of the surface of the glans penis and to provide clitoral stimulation during coitus.

25. The prophylactic pouch of claim 22 characterized by the second pouch being coated with a lubricant to provide a hydrodynamic rubbing of the glans penis.

26. The prophylactic pouch of claim 25 characterized by the lubricant being a water soluble lubricant.

27. The prophylactic pouch of claim 22, further characterized by said second pouch comprising a row of pouches spaced longitudinally on said tubular portion and operable to move on and stimulate the penis and to simultaneously massage and stimulate the clitoris of a female partner during coitus.

28. The prophylactic pouch of claim 22, further characterized by said second pouch comprising two radially opposite rows of pouches spaced longitudinally on said tubular portion circumferentially spaced by portions of said tubular portion maintaining said constant diameter throughout the length of said tubular portion by resisting stretching of said tubular portion to thereby maintain the shape of said rows of pouches to assure stimulation of the glans penis and enable massaging and resultant stimulation of the clitoris of a female partner during coitus.

29. The prophylactic pouch of claim 28, further characterized by at least the pouches overlying the glans penis containing a coating of a lubricant to provide hydrodynamic rubbing of the glans penis during pouch movement.

30. The prophylactic pouch of claim 29, further characterized by the lubricant being a water soluble lubricant.

31. A prophylactic pouch for use by a male, having an elongated tubular portion forming a first pouch including a circumference, an open end and a closed end, said tubular portion having a generally constant diameter from end to end, characterized by:

a second pouch integrally formed on the circumference of said tubular portion as an outward bulge on the closed end in overlying spaced relationship to a glans penis and operable to move thereon to provide stimulation during coitus; said second pouch formed of thin membrane material extending outwardly of said first pouch; said second pouch having an interior space and including an entrance with an open area extending lengthwise of the glans penis at least 1 cm; said entrance communicating said interior space directly with said longitudinally directed chamber at a point overlying the glans penis; said second pouch having an inner surface moveable through said entrance and against the glans penis for movement.

32. The prophylactic pouch of claim 31, further characterized by:

a third pouch formed as an outward bulge intermediate the open and closed end for engaging and stimulating the clitoris of a female partner during coitus.

33. The prophylactic pouch of claim 32, further characterized by the pouch overlying the glans penis containing a coating of a lubricant to provide hydrodynamic rubbing of the glans penis during pouch movement.

34. The prophylactic pouch of claim 32, further characterized by:
   said second pouch comprising a row of longitudinally spaced pouches formed as outward bulges on the circumference of the tubular portion; and
   said tubular portion including one longitudinal portion maintaining said constant diameter to resist stretching of the tubular portion to thereby maintain the shape of said pouches and assure both glans penis and clitoral stimulation during coitus.

35. The prophylactic pouch of claim 32, further characterized by:
   said second pouch comprising two rows of longitudinally spaced pouches formed on the surface of said tubular portion; and
   said rows of pouches being circumferentially spaced and separate by longitudinal portions of said tubular portion maintaining said constant diameter to resist stretching of said tubular portion to thereby maintain the shape of said pouches and assure both glans penis and clitoral stimulation during coitus.

36. The prophylactic pouch of claim 32, further characterized by:
   at least those pouches overlying the glans penis containing a coating of a lubricant to provide hydrodynamic rubbing of the glans penis during pouch movement.

* * * * *